US012011259B2

(12) United States Patent
Dohrmann et al.

(10) Patent No.: US 12,011,259 B2
(45) Date of Patent: Jun. 18, 2024

(54) SYSTEMS AND METHODS FOR FALL DETECTION (71) Applicant: Electronic Caregiver, Inc., Las Cruces, NM (US)

(72) Inventors: Anthony Dohrmann, Las Cruces, NM (US); David W. Keeley, Frisco, TX (US); Roberto Abel Salcido, Las Cruces, NM (US); James Mitchell, Las Cruces, NM (US)

(73) Assignee: ELECTRONIC CAREGIVER, INC., Las Cruces, NM (US)

(*) Notice: Subject to any disclaimer, the term of this patent is extended or adjusted under 35 U.S.C. 154(b) by 674 days.

(21) Appl. No.: 17/013,357

(22) Filed: Sep. 4, 2020

(65) Prior Publication Data
US 2021/0007631 A1    Jan. 14, 2021

Related U.S. Application Data (63) Continuation of application No. 15/530,185, filed on Dec. 9, 2016, now Pat. No. 10,813,572.
(Continued)

(51) Int. Cl.
*A61B 5/00* (2006.01)
*A61B 5/103* (2006.01)
(Continued)

(52) U.S. Cl.
CPC .......... *A61B 5/1117* (2013.01); *A61B 5/0013* (2013.01); *A61B 5/0077* (2013.01);
(Continued)

(58) Field of Classification Search
CPC ..... G06F 3/015; A61B 5/0077; A61B 5/1114; A61B 5/224; A61B 5/30; A61B 5/4528;
(Continued)

(56) References Cited

U.S. PATENT DOCUMENTS 5,211,642 A    5/1993  Clendenning
5,475,953 A   12/1995  Greenfield
(Continued)

FOREIGN PATENT DOCUMENTS

AU    2019240484 B2   11/2021
CA       2949449 A1   11/2015
(Continued)

OTHER PUBLICATIONS

"International Search Report" and "Written Opinion of the International Searching Authority," Patent Cooperation Treaty Application No. PCT/US2018/057814, dated Jan. 11, 2019, 9 pages.
(Continued)

*Primary Examiner* — May A Abouelela
(74) *Attorney, Agent, or Firm* — Carr & Ferrell, LLP (57) ABSTRACT A system for monitoring and detecting the gait and other health related parameters of a user. One such parameter is monitoring of medication compliance and treatment session attendance done by a medication and liquid dispensing apparatus, which combines mechanical dispensing of medication. These parameters are provided in standard of care summaries to care providers, and are continually reported by the Optimum Recognition Blueprint as Standard of Care Summaries to care providers, as well as communicated to the end-user by the Virtual Caregiver Interface.

20 Claims, 8 Drawing Sheets

Related U.S. Application Data (60) Provisional application No. 62/386,768, filed on Dec. 11, 2015.

(51) Int. Cl.
  *A61B 5/11* (2006.01)
  *A61B 5/1171* (2016.01)
  *A61B 5/0205* (2006.01)

(52) U.S. Cl.
  CPC .......... *A61B 5/1036* (2013.01); *A61B 5/1127* (2013.01); *A61B 5/1128* (2013.01); *A61B 5/1176* (2013.01); *A61B 5/4833* (2013.01); *A61B 5/4866* (2013.01); *A61B 5/7275* (2013.01); *A61B 5/746* (2013.01); *A61B 5/749* (2013.01); *A61B 5/02055* (2013.01)

(58) Field of Classification Search
  CPC ... A61B 5/6802; A61B 5/742; A61B 2505/09; A61B 5/0022; A61B 5/1128; A61B 5/257; A61B 5/458; A61B 5/4585; A61B 5/313; A61B 5/7225; A61B 2560/0214; A61B 5/1123; A61B 2562/0219; A61B 5/1122; A61B 5/486; A61B 2562/164; A61B 5/1495; A61B 5/1117; A61B 5/0013; A61B 5/1036; A61B 5/1127; A61B 5/1176; A61B 5/4833; A61B 5/4866; A61B 5/7275; A61B 5/746; A61B 5/749; A61B 5/02055
  See application file for complete search history.

(56) References Cited

U.S. PATENT DOCUMENTS

| | | | |
|---|---|---|---|
| 6,665,647 B1 | 12/2003 | Haudenschild | |
| 7,233,872 B2 | 6/2007 | Shibasaki et al. | |
| 7,445,086 B1 | 11/2008 | Sizemore | |
| 7,612,681 B2 | 11/2009 | Azzaro et al. | |
| 7,971,141 B1 | 6/2011 | Quinn et al. | |
| 8,206,325 B1 | 6/2012 | Najafi et al. | |
| 8,771,206 B2* | 7/2014 | Gettelman | A61B 5/744 600/595 |
| 9,072,929 B1 | 7/2015 | Rush et al. | |
| 9,317,916 B1 | 4/2016 | Hanina et al. | |
| 9,591,996 B2 | 3/2017 | Chang et al. | |
| 9,972,187 B1 | 5/2018 | Srinivasan et al. | |
| 10,387,963 B1 | 8/2019 | Leise et al. | |
| 10,417,388 B2 | 9/2019 | Han et al. | |
| 10,628,635 B1 | 4/2020 | Carpenter, II et al. | |
| 10,761,691 B2 | 9/2020 | Anzures et al. | |
| 10,813,572 B2 | 10/2020 | Dohrmann et al. | |
| 10,943,407 B1 | 3/2021 | Morgan et al. | |
| 11,113,943 B2 | 9/2021 | Wright et al. | |
| 11,213,224 B2 | 1/2022 | Dohrmann et al. | |
| 2002/0062342 A1 | 5/2002 | Sidles | |
| 2002/0196944 A1 | 12/2002 | Davis et al. | |
| 2004/0109470 A1 | 6/2004 | Derechin et al. | |
| 2005/0035862 A1* | 2/2005 | Wildman | G08B 13/2462 340/572.1 |
| 2005/0055942 A1 | 3/2005 | Maelzer et al. | |
| 2007/0238936 A1 | 10/2007 | Becker | |
| 2008/0010293 A1 | 1/2008 | Zpevak et al. | |
| 2008/0186189 A1 | 8/2008 | Azzaro et al. | |
| 2009/0094285 A1 | 4/2009 | Mackle et al. | |
| 2010/0124737 A1 | 5/2010 | Panzer | |
| 2011/0126207 A1* | 5/2011 | Wipfel | H04L 63/08 718/104 |
| 2011/0145018 A1 | 6/2011 | Fotsch et al. | |
| 2011/0232708 A1 | 9/2011 | Kemp | |
| 2012/0025989 A1* | 2/2012 | Cuddihy | G08B 21/0476 382/106 |
| 2012/0075464 A1* | 3/2012 | Derenne | A61B 5/0036 600/595 |
| 2012/0120184 A1 | 5/2012 | Fornell et al. | |
| 2012/0121849 A1 | 5/2012 | Nojima | |
| 2012/0154582 A1 | 6/2012 | Johnson et al. | |
| 2012/0165618 A1 | 6/2012 | Algoo et al. | |
| 2012/0179067 A1* | 7/2012 | Wekell | A61B 5/6831 600/587 |
| 2012/0179916 A1 | 7/2012 | Staker et al. | |
| 2012/0229634 A1* | 9/2012 | Laett | G16H 40/67 348/143 |
| 2012/0253233 A1 | 10/2012 | Greene et al. | |
| 2013/0000228 A1 | 1/2013 | Ovaert | |
| 2013/0127620 A1* | 5/2013 | Siebers | A61B 5/1113 340/573.1 |
| 2013/0145449 A1 | 6/2013 | Busser et al. | |
| 2013/0167025 A1 | 6/2013 | Patri et al. | |
| 2013/0204545 A1 | 8/2013 | Solinsky | |
| 2013/0212501 A1 | 8/2013 | Anderson et al. | |
| 2013/0237395 A1* | 9/2013 | Hjelt | A63B 22/18 482/146 |
| 2013/0289449 A1* | 10/2013 | Stone | A61B 5/0013 600/595 |
| 2013/0303860 A1 | 11/2013 | Bender et al. | |
| 2014/0074454 A1 | 3/2014 | Brown et al. | |
| 2014/0128691 A1 | 5/2014 | Olivier | |
| 2014/0148733 A1* | 5/2014 | Stone | A61B 5/0077 600/595 |
| 2014/0171039 A1 | 6/2014 | Bjontegard | |
| 2014/0171834 A1 | 6/2014 | DeGoede et al. | |
| 2014/0232600 A1* | 8/2014 | Larose | G01S 5/06 342/463 |
| 2014/0243686 A1* | 8/2014 | Kimmel | A61B 5/1114 600/407 |
| 2014/0257852 A1 | 9/2014 | Walker et al. | |
| 2014/0267582 A1 | 9/2014 | Beutter et al. | |
| 2014/0278605 A1 | 9/2014 | Borucki et al. | |
| 2014/0330172 A1 | 11/2014 | Jovanov et al. | |
| 2014/0337048 A1 | 11/2014 | Brown et al. | |
| 2014/0343460 A1* | 11/2014 | Evans, III | A61B 5/112 600/595 |
| 2014/0358828 A1 | 12/2014 | Phillipps et al. | |
| 2014/0368601 A1 | 12/2014 | deCharms | |
| 2015/0019250 A1 | 1/2015 | Goodman et al. | |
| 2015/0109442 A1* | 4/2015 | Derenne | H04N 7/185 348/143 |
| 2015/0169835 A1 | 6/2015 | Hamdan et al. | |
| 2015/0359467 A1 | 12/2015 | Tran | |
| 2016/0026354 A1 | 1/2016 | Mcintosh et al. | |
| 2016/0117470 A1 | 4/2016 | Welsh et al. | |
| 2016/0117484 A1 | 4/2016 | Hanina et al. | |
| 2016/0125620 A1* | 5/2016 | Heinrich | G06F 18/2431 382/103 |
| 2016/0154977 A1 | 6/2016 | Jagadish et al. | |
| 2016/0217264 A1 | 7/2016 | Sanford | |
| 2016/0253890 A1 | 9/2016 | Rabinowitz et al. | |
| 2016/0267327 A1 | 9/2016 | Franz et al. | |
| 2016/0314255 A1 | 10/2016 | Cook et al. | |
| 2017/0000387 A1 | 1/2017 | Forth et al. | |
| 2017/0000422 A1 | 1/2017 | Moturu et al. | |
| 2017/0024531 A1 | 1/2017 | Malaviya | |
| 2017/0055917 A1 | 3/2017 | Stone et al. | |
| 2017/0140631 A1 | 5/2017 | Pietrocola et al. | |
| 2017/0147154 A1* | 5/2017 | Steiner | G06F 3/013 |
| 2017/0189751 A1 | 7/2017 | Knickerbocker et al. | |
| 2017/0192950 A1 | 7/2017 | Gaither et al. | |
| 2017/0193163 A1 | 7/2017 | Melle et al. | |
| 2017/0197115 A1 | 7/2017 | Cook et al. | |
| 2017/0213145 A1 | 7/2017 | Pathak et al. | |
| 2017/0273601 A1 | 9/2017 | Wang et al. | |
| 2017/0337274 A1 | 11/2017 | Ly et al. | |
| 2017/0344706 A1 | 11/2017 | Torres et al. | |
| 2017/0344832 A1 | 11/2017 | Leung et al. | |
| 2018/0005448 A1 | 1/2018 | Choukroun et al. | |
| 2018/0075558 A1 | 3/2018 | Hill, Sr. et al. | |
| 2018/0096504 A1 | 4/2018 | Valdivia et al. | |
| 2018/0154514 A1 | 6/2018 | Angle et al. | |
| 2018/0165938 A1 | 6/2018 | Honda et al. | |
| 2018/0182472 A1 | 6/2018 | Preston et al. | |
| 2018/0189756 A1 | 7/2018 | Purves et al. | |

(56) References Cited

U.S. PATENT DOCUMENTS

| | | |
|---|---|---|
| 2018/0322405 A1 | 11/2018 | Fadell et al. |
| 2018/0330810 A1 | 11/2018 | Gamarnik et al. |
| 2018/0360349 A9 | 12/2018 | Dohrmann et al. |
| 2018/0365759 A1 | 12/2018 | Balzer et al. |
| 2018/0368780 A1 | 12/2018 | Bruno et al. |
| 2019/0029900 A1 | 1/2019 | Walton et al. |
| 2019/0042700 A1 | 2/2019 | Alotaibi |
| 2019/0057320 A1 | 2/2019 | Docherty et al. |
| 2019/0090786 A1 | 3/2019 | Kim et al. |
| 2019/0116212 A1 | 4/2019 | Spinella-Mamo |
| 2019/0130110 A1 | 5/2019 | Lee et al. |
| 2019/0156575 A1 | 5/2019 | Korhonen |
| 2019/0164015 A1 | 5/2019 | Jones, Jr. et al. |
| 2019/0196888 A1 | 6/2019 | Anderson et al. |
| 2019/0220727 A1 | 7/2019 | Dohrmann et al. |
| 2019/0259475 A1 | 8/2019 | Dohrmann et al. |
| 2019/0282130 A1 | 9/2019 | Dohrmann et al. |
| 2019/0286942 A1 | 9/2019 | Abhiram et al. |
| 2019/0311792 A1 | 10/2019 | Dohrmann et al. |
| 2019/0318165 A1 | 10/2019 | Shah et al. |
| 2019/0385749 A1 | 12/2019 | Dohrmann et al. |
| 2020/0043594 A1 | 2/2020 | Miller et al. |
| 2020/0101969 A1 | 4/2020 | Natroshvili et al. |
| 2020/0129107 A1 | 4/2020 | Sharma et al. |
| 2020/0236090 A1 | 7/2020 | De Beer et al. |
| 2020/0251220 A1 | 8/2020 | Chasko |
| 2020/0357256 A1 | 11/2020 | Wright et al. |
| 2020/0357511 A1 | 11/2020 | Sanford |
| 2021/0016150 A1 | 1/2021 | Jeong et al. |
| 2021/0110894 A1 | 4/2021 | Shriberg et al. |
| 2021/0134456 A1 | 5/2021 | Posnack et al. |
| 2021/0273962 A1 | 9/2021 | Dohrmann et al. |
| 2021/0358202 A1 | 11/2021 | Tveito et al. |
| 2021/0375426 A1 | 12/2021 | Gobezie et al. |
| 2021/0398410 A1 | 12/2021 | Wright et al. |
| 2022/0022760 A1 | 1/2022 | Salcido et al. |
| 2022/0031199 A1 | 2/2022 | Hao et al. |
| 2022/0157427 A1 | 5/2022 | Keeley et al. |
| 2022/0319696 A1 | 10/2022 | Dohrmann et al. |
| 2022/0319713 A1 | 10/2022 | Dohrmann et al. |
| 2022/0319714 A1 | 10/2022 | Dohrmann et al. |
| 2023/0108601 A1 | 4/2023 | Coelho Alves et al. |

FOREIGN PATENT DOCUMENTS

| | | |
|---|---|---|
| CN | 104361321 A | 2/2015 |
| CN | 106056035 A | 10/2016 |
| CN | 107411515 A | 12/2017 |
| CN | 111801645 A | 10/2020 |
| CN | 111801939 A | 10/2020 |
| CN | 111867467 A | 10/2020 |
| CN | 113795808 | 12/2021 |
| EP | 3740856 A1 | 11/2020 |
| EP | 3756344 A1 | 12/2020 |
| EP | 3768164 A1 | 1/2021 |
| EP | 3773174 A1 | 2/2021 |
| EP | 3815108 A1 | 5/2021 |
| EP | 3920797 A1 | 12/2021 |
| EP | 3944258 | 1/2022 |
| EP | 3966657 A | 3/2022 |
| IN | 202027033318 A | 10/2020 |
| IN | 202027035634 A | 10/2020 |
| JP | 2002304362 A | 10/2002 |
| JP | 2005228305 A | 8/2005 |
| JP | 2010172481 A | 8/2010 |
| JP | 2012232652 A | 11/2012 |
| JP | 2016137226 A | 8/2016 |
| JP | 2016525383 A | 8/2016 |
| KR | 1020160040078 A | 4/2016 |
| KR | 1020200105519 A | 9/2020 |
| KR | 1020200121832 A | 10/2020 |
| KR | 1020200130713 A | 11/2020 |
| WO | WO2000005639 A2 | 2/2000 |
| WO | WO2014043757 A1 | 3/2014 |
| WO | WO2017118908 A1 | 7/2017 |
| WO | WO2018032089 A1 | 2/2018 |
| WO | WO2019143397 A1 | 7/2019 |
| WO | WO2019164585 A1 | 8/2019 |
| WO | WO2019182792 A1 | 9/2019 |
| WO | WO2019199549 A1 | 10/2019 |
| WO | WO2019245713 A1 | 12/2019 |
| WO | WO2020163180 A1 | 8/2020 |
| WO | WO2020227303 A1 | 11/2020 |

OTHER PUBLICATIONS

"International Search Report" and "Written Opinion of the International Searching Authority," Patent Cooperation Treaty Application No. PCT/US2018/068210, dated Apr. 12, 2019, 9 pages.

"International Search Report" and "Written Opinion of the International Searching Authority," Patent Cooperation Treaty Application No. PCT/US2019/021678, dated May 24, 2019, 12 pages.

"International Search Report" and "Written Opinion of the International Searching Authority," Patent Cooperation Treaty Application No. PCT/US2019/025652, dated Jul. 18, 2019, 11 pages.

"International Search Report" and "Written Opinion of the International Searching Authority," Patent Cooperation Treaty Application No. PCT/US2019/034206, dated Aug. 1, 2019, 11 pages.

Rosen et al., "Slipping and Tripping: Fall Injuries in Adults Associated with Rugs and Carpets," Journal of Injury & Violence Research, 5(1), (2013), pp. 61-69.

Bajaj, Prateek, "Reinforcement Learning", GeeksForGeeks.org [online], [retrieved on Mar. 4, 2020], Retrieved from the Internet:<URL:https://www.geeksforgeeks.org/what-is-reinforcement-learning/>, 7 pages.

Kung-Hsiang, Huang (Steeve), "Introduction to Various RL Algorithms. Part I (Q-Learning, SARSA, DQN, DDPG)", Towards Data Science, [online], [retrieved on Mar. 4, 2020], Retrieved from the Internet:<URL:https://towardsdatascience.com/introduction-to-various-reinforcement-learning-algorithms-i-q-learning-sarsa-dqn-ddpg-72a5e0cb6287>, 5 pages.

Bellemare et al., A Distributional Perspective on Reinforcement Learning:, Proceedings of the 34th International Conference on Machine Learning, Sydney, Australia, Jul. 21, 2017, 19 pages.

Friston et al., "Reinforcement Learning or Active Inference?" Jul. 29, 2009, [online], [retrieved on Mar. 4, 2020], Retrieved from the Internet:<URL:https://doi.org/10.1371/journal.pone.0006421 PLoS ONE 4(7): e6421>, 13 pages.

Zhang et al., "DQ Scheduler: Deep Reinforcement Learning Based Controller Synchronization in Distributed SDN" ICC 2019—2019 IEEE International Conference on Communications (ICC), Shanghai, China, doi: 10.1109/ICC.2019.8761183, pp. 1-7.

"International Search Report" and "Written Opinion of the International Searching Authority," Patent Cooperation Treaty Application No. PCT/US2020/031486, dated Aug. 3, 2020, 7 pages.

"International Search Report" and "Written Opinion of the International Searching Authority," Patent Cooperation Treaty Application No. PCT/US2020/016248, dated May 11, 2020, 7 pages.

"Office Action", Australia Patent Application No. 2019240484, dated Nov. 13, 2020, 4 pages.

"Office Action", Australia Patent Application No. 2018403182, dated Feb. 5, 2021, 5 pages.

"Office Action", Australia Patent Application No. 2018409860, dated Feb. 10, 2021, 4 pages.

Leber, Jessica, "The Avatar Will See You Now", MIT Technology Review, Sep. 17, 2013, 4 pages.

"Office Action", India Patent Application No. 202027035634, dated Jun. 30, 2021, 10 pages.

"Office Action", India Patent Application No. 202027033121, dated Jul. 29, 2021, 7 pages.

"Office Action", Canada Patent Application No. 3088396, dated Aug. 6, 2021, 7 pages.

"Office Action", China Patent Application No. 201880089608.2, dated Aug. 3, 2021, 8 pages.

"Office Action", Japan Patent Application No. 2020-543924, dated Jul. 27, 2021, 3 pages [6 pages with translation].

"Office Action", Australia Patent Application No. 2019240484, dated Aug. 2, 2021, 3 pages.

(56) References Cited

OTHER PUBLICATIONS

"Office Action", Canada Patent Application No. 3089312, dated Aug. 19, 2021, 3 pages.
"Extended European Search Report", European Patent Application No. 18901139.8, dated Sep. 9, 2021, 6 pages.
"Office Action", Canada Patent Application No. 3091957, dated Sep. 14, 2021, 4 pages.
"Office Action", Japan Patent Application No. 2020-540382, dated Aug. 24, 2021, 7 pages [13 pages with translation].
"Extended European Search Report", European Patent Application No. 18907032.9, dated Oct. 15, 2021, 12 pages.
Marston et al., "The design of a purpose-built exergame for fall prediction and prevention for older people", European Review of Aging and Physical Activity 12:13, <URL:https://eurapa.biomedcentral.com/track/pdf/10.1186/s11556-015-0157-4.pdf>, Dec. 8, 2015, 12 pages.
Ejupi et al., "Kinect-Based Five-Times-Sit-to-Stand Test for Clinical and In-Home Assessment of Fall Risk in Older People", Gerontology (vol. 62), (May 25, 2015), <URL:https://www.karger.com/Article/PDF/381804>, May 28, 2015, 7 pages.
Festl et al., "iStoppFalls: A Tutorial Concept and prototype Contents". <URL:https://hcisiegen.de/wp-uploads/2014/05/isCtutorialdoku.pdf>, Mar. 30, 2013, 36 pages.
"Notice of Allowance", Australia Patent Application No. 2019240484, dated Oct. 27, 2021, 4 pages.
"Extended European Search Report", European Patent Application No. 19772545.0, dated Nov. 16, 2021, 8 pages.
"Office Action", India Patent Application No. 202027033318, dated Nov. 18, 2021, 6 pages.
"Office Action", Australia Patent Application No. 2018409860, dated Nov. 30, 2021, 4 pages.
"Office Action", Australia Patent Application No. 2018403182, dated Dec. 1, 2021, 3 pages.
"Office Action", Korea Patent Application No. 10-2020-7028606, dated Oct. 29, 2021, 7 pages [14 pages with translation].
"Office Action", Japan Patent Application No. 2020-543924, dated Nov. 24, 2021, 3 pages [6 pages with translation].
"Extended European Search Report", European Patent Application No. EP19785057, dated Dec. 6, 2021, 8 pages.
"Office Action", Australia Patent Application No. 2020218172, dated Dec. 21, 2021, 4 pages.
"Extended European Search Report", European Patent Application No. 21187314.6, dated Dec. 10, 2021, 10 pages.
"Notice of Allowance", Australia Patent Application No. 2018403182, dated Jan. 20, 2022, 4 pages.
"Office Action", Australia Patent Application No. 2018409860, dated Jan. 24, 2022, 5 pages.
"Office Action", China Patent Application No. 201880089608.2, dated Feb. 8, 2022, 6 pages (15 pages with translation),.
"International Search Report" and "Written Opinion of the International Searching Authority," Patent Cooperation Treaty Application No. PCT/US2021/056060, dated Jan. 28, 2022, 8 pages.
"Extended European Search Report", European Patent Application No. 19822930.4, dated Feb. 15, 2022, 9 pages.
"Office Action", Japan Patent Application No. 2020-550657, dated Feb. 8, 2022, 8 pages.

* cited by examiner

SYSTEMS AND METHODS FOR FALL DETECTION

PRIORITY

This continuation application claims the priority benefit of U.S. Non-Provisional patent application Ser. No. 15/530,185 filed on Dec. 9, 2016, titled "Intelligent System for Multi-Function Electronic Caregiving to Facilitate Advanced Health Diagnosis, Health Monitoring, Fall and Injury Prediction, Health Maintenance and Support, and Emergency Response," which in turn claims the priority benefit of U.S. Provisional Patent Application Ser. No. 62/386,768, filed on Dec. 11, 2015, titled "Intelligent System for Multi-Function Electronic Caregiving to Facilitate Advanced Health Diagnosis, Health Monitoring, Fall and Injury Prediction, Health Maintenance and Support, and Emergency Response," and of which are incorporated by reference in their entireties.

BACKGROUND OF THE INVENTION

Field of the Invention

This invention relates to a system of automated electronic caregiving assistance and health monitoring.

Description of the Prior Art

In recent years, personal emergency response systems ("PERS") have been developed which offer a single button, worn or the wrist, a belt or around the neck, which allows a user to summon help during an emergency. Other PERS have been developed that include connections with external systems, such as a central monitoring center. These types of PERS, however, do not include robust methods of communication, the capability to scale with the addition of new subsystems, advanced methods of sensing or detection, comprehensive analytical capability, or clinically useful feedback.

SUMMARY OF THE INVENTION

It is, therefore, an object of the present invention to provide for more effective monitoring of key indicators that will allow more reliable early warning to reduce loss of life, medical complications, pain, suffering, loss of independence, and medical costs. This invention aims to supplement and/or replace live caregivers and nurses by substantially improving and expanding continual oversight and quality of care, resulting in promotion of early intervention and expedited response during emergencies, and to assess and evaluate methods of care and their impact on patient improvement, stability, or decline. The invention will improve access to knowledge and care for both care providers and end-users of the invention. Other objects and advantages of the present invention will become apparent from the following detailed description when viewed in conjunction with the accompanying drawings, which set forth certain embodiments of the invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention.

The present invention has been developed in response to the contemporary state of health monitoring. Problems and needs requiring health monitoring have not yet been fully solved by currently available PERS. The present invention is intended to provide a comprehensive method of electronic caregiving support, health oversight and emergency response. The benefits to families and individuals seeking these protections are amplified for those who are at high risk, chronically ill, physically impaired, mentally impaired, or rehabilitating end users.

The present invention includes a front end Electronic Caregiver system of sensing devices and user interaction, and a back end Electronic Caregiver system providing an automated process to navigate responses to situations on the front end system. The Electronic Caregiver may interface with portable devices such as a tablet, a wearable device, or a mobile phone, all of which may be equipped with accelerometers, gyroscopic or movement sensors, or microprocessors. Software applications on the portable devices will maximize the capability of the Electronic Caregiver back end system and be capable of displaying updated information received from such back-end system as well as initiating other algorithms, programs and processes.

For example, in a home safety and health monitoring system, a network of devices transmit information relating to an individual's physics, gait, activity, inactivity, metal behavior, and health activities to the Electronic Caregiver system. These devices may include biomechanical detection sensors, wearable accelerometers, gyroscopic. sensors, tilt sensors, visual analytical monitoring devices, wireless ubiquitous monitoring devices, under foot pressure sensors, all of which will provide the back end of the Electronic Caregiver system data that can be assigned a biomechanical meaning. The front end of the Electronic Caregiver system will then communicate notifications and other feed back to the end user or external parties such as central monitoring stations, health providers, and/or family members.

Figure 1:
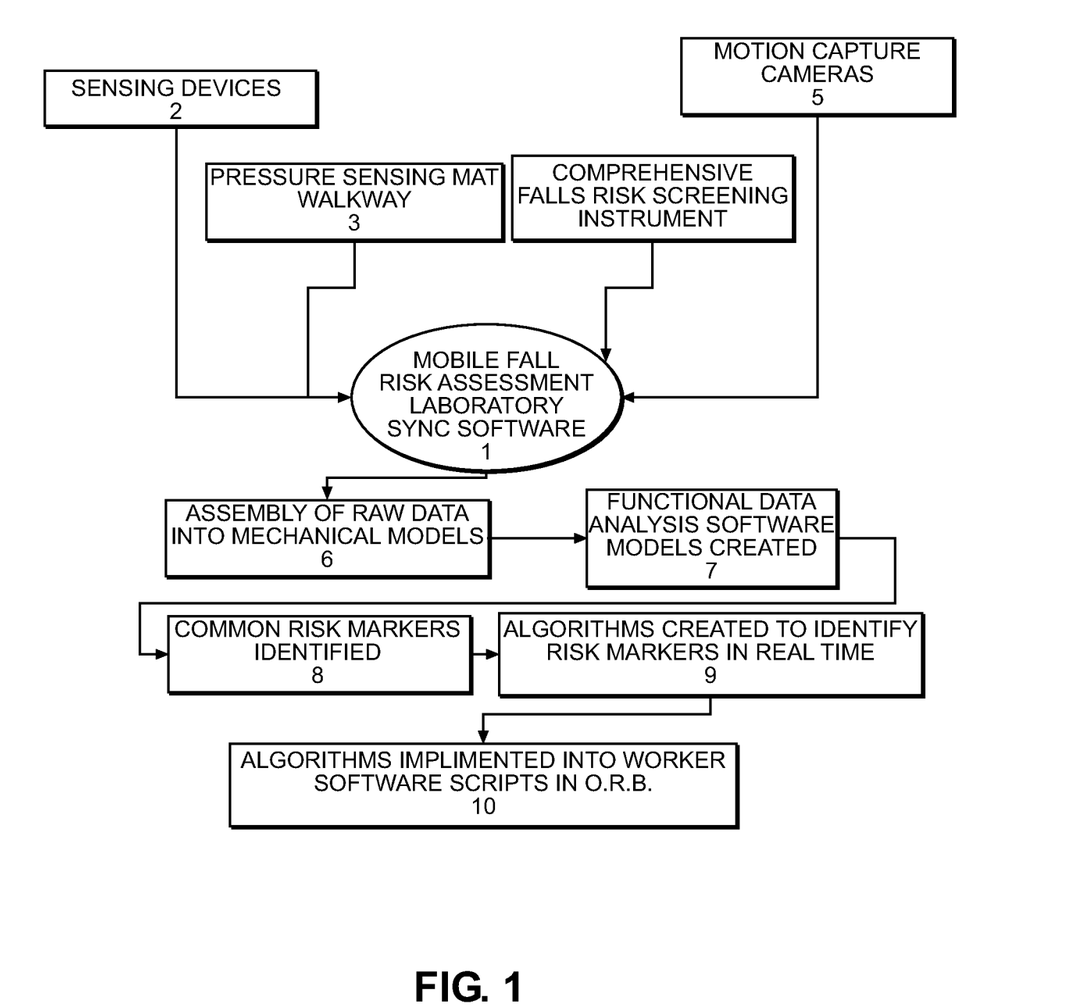
FIG. 1 is a flow chart showing the process necessary to create risk scores for new devices utilizing a golden standard of established methodology.
Figure 2:
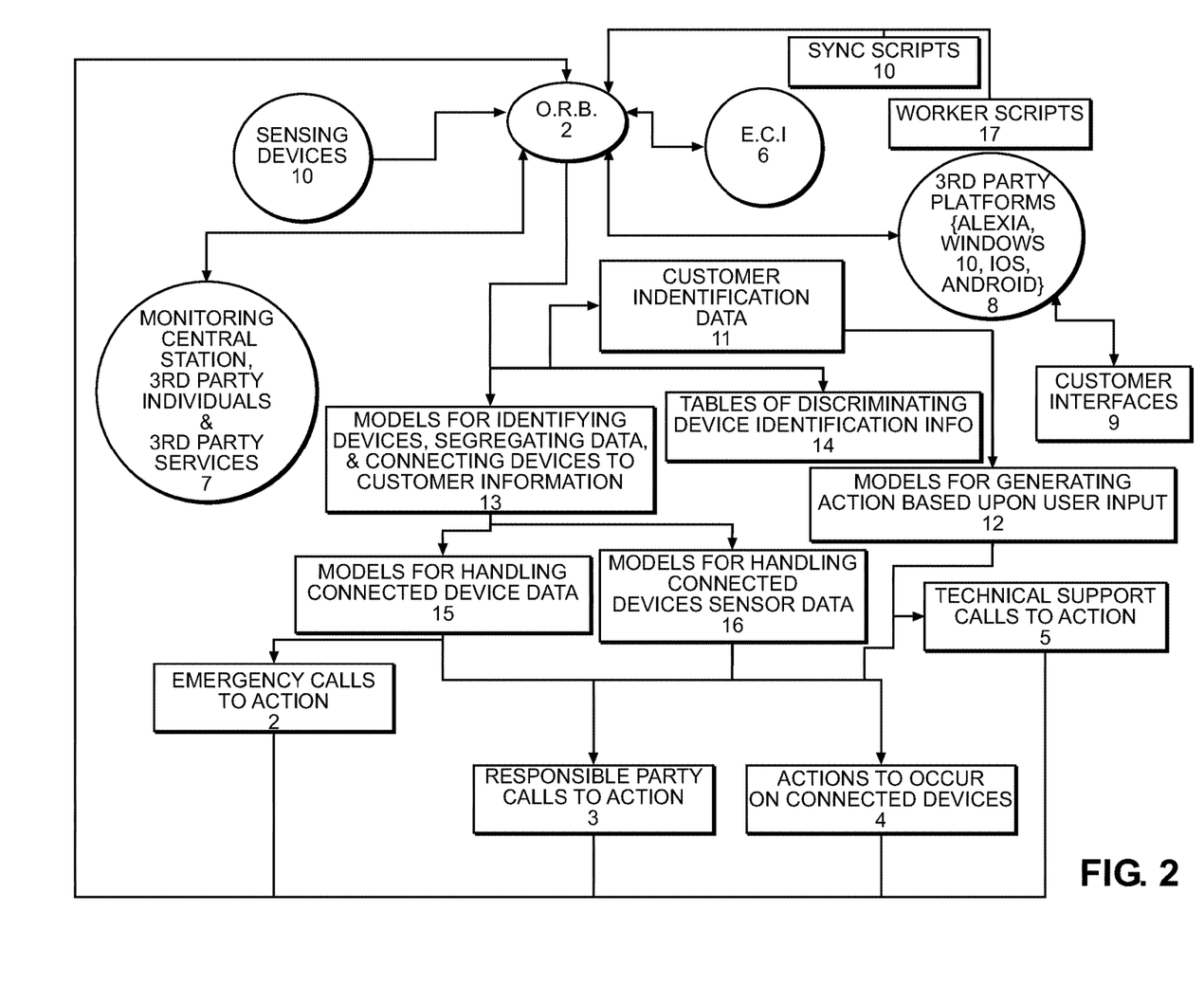
FIG. 2 is a flow chart showing the process for properly handling information from a variety of sensing devices across a variety of platforms via the Electronic Caregiver Optimum Recognition Blueprint.
Figure 3A:
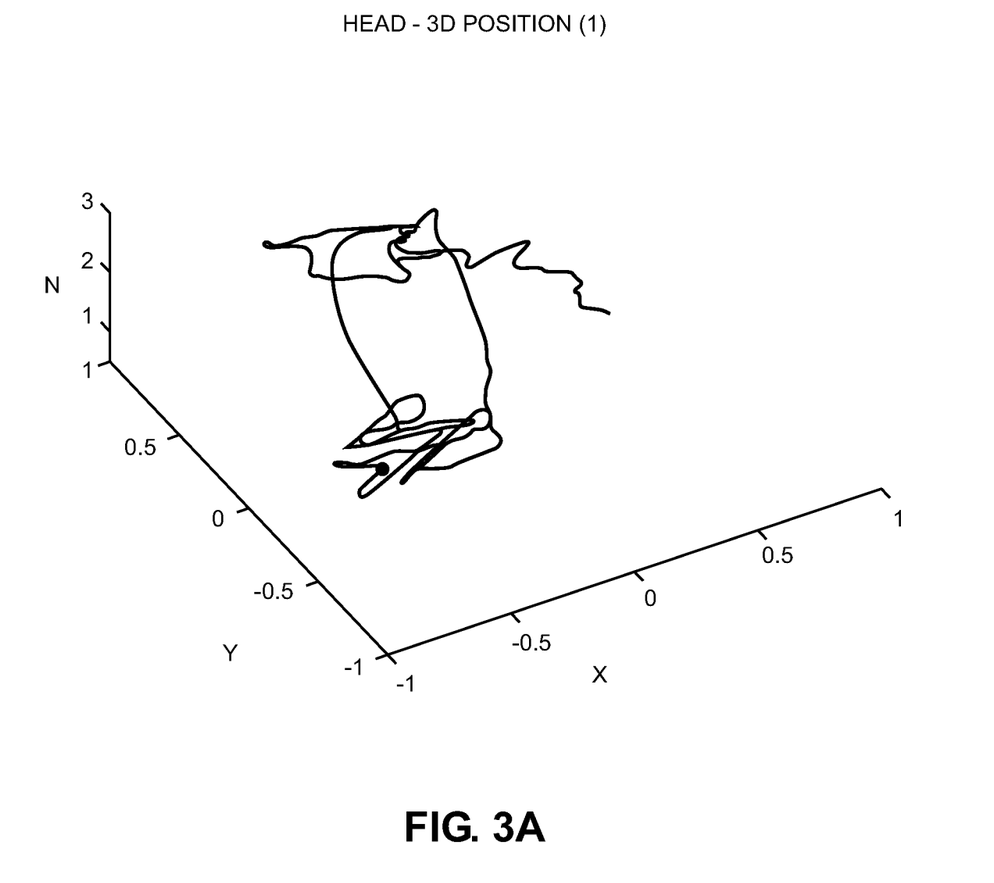
FIGS. 3A-3D illustrate the tracking of head movement during a fall as captured from a depth camera.
Figure 3B:
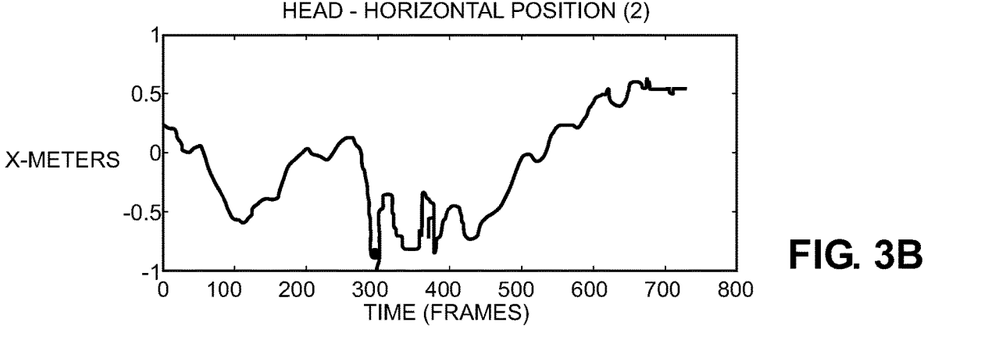
Figure 3C:
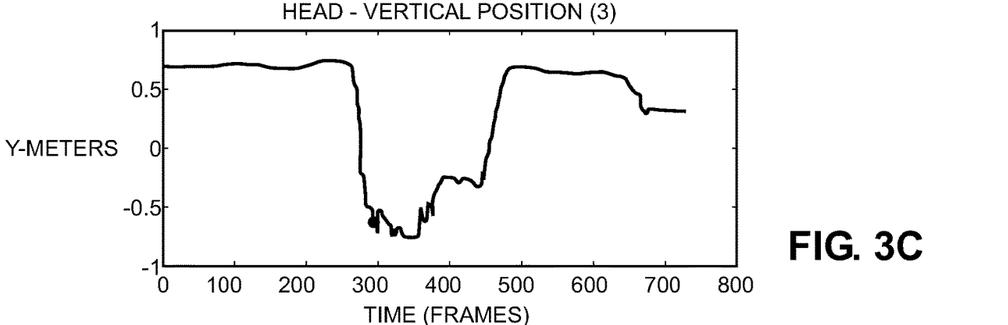
Figure 3D:
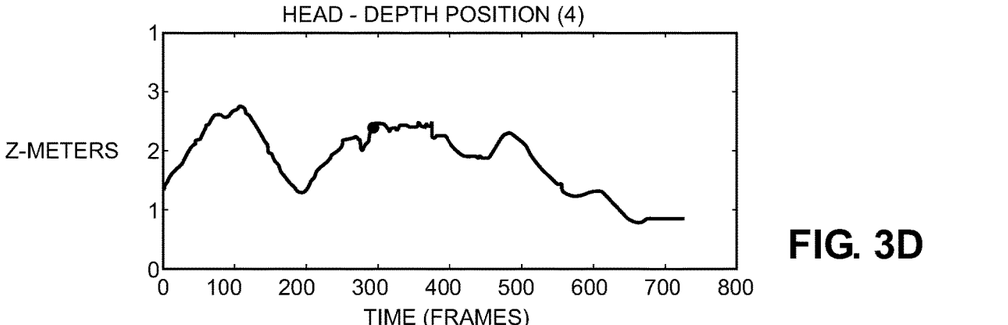
Figure 4A:
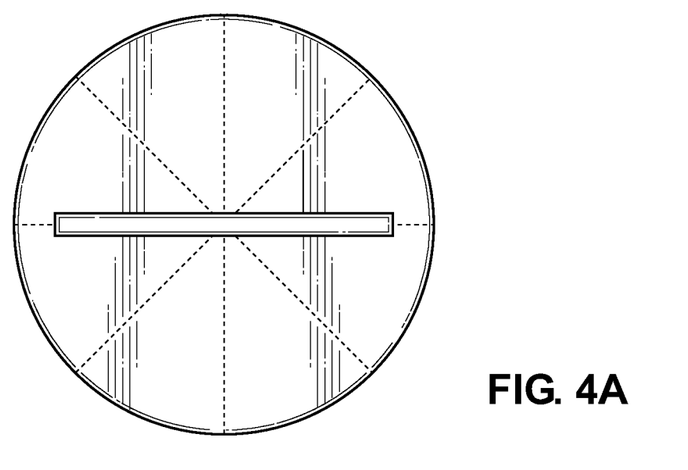
FIGS. 4A-4C are drawings of a pill box that dispenses appropriate amounts of medications at prescribed times, featuring a camera that sends data to the Electronic Caregiver Optimum Recognition Blueprint for visual analytics. This version includes a tablet for visual display of the Electronic Caregiver Image.
Figure 4B:
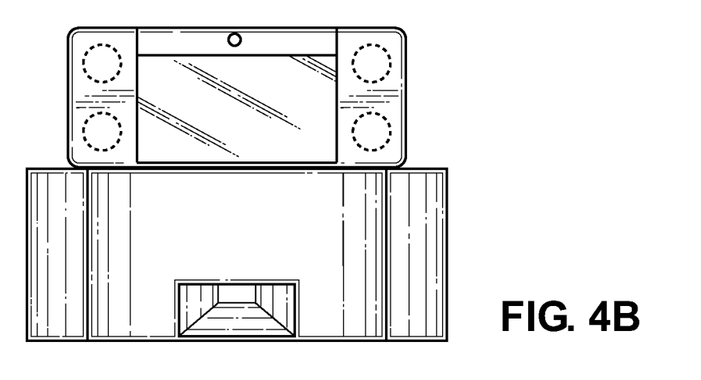
Figure 4C:
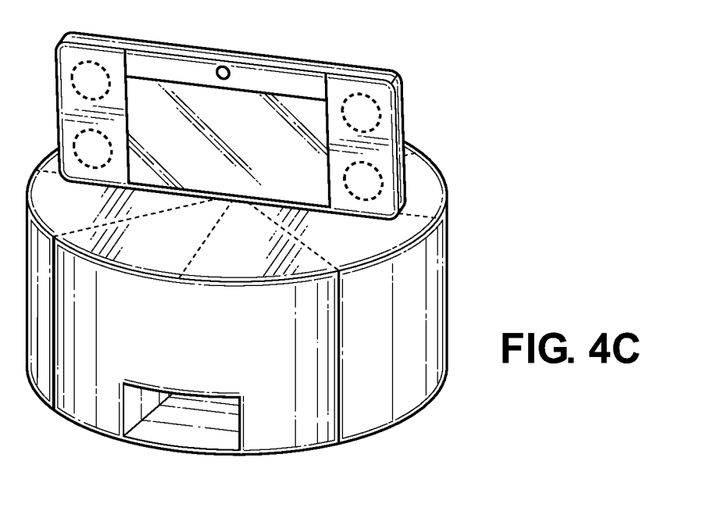
Figure 5:
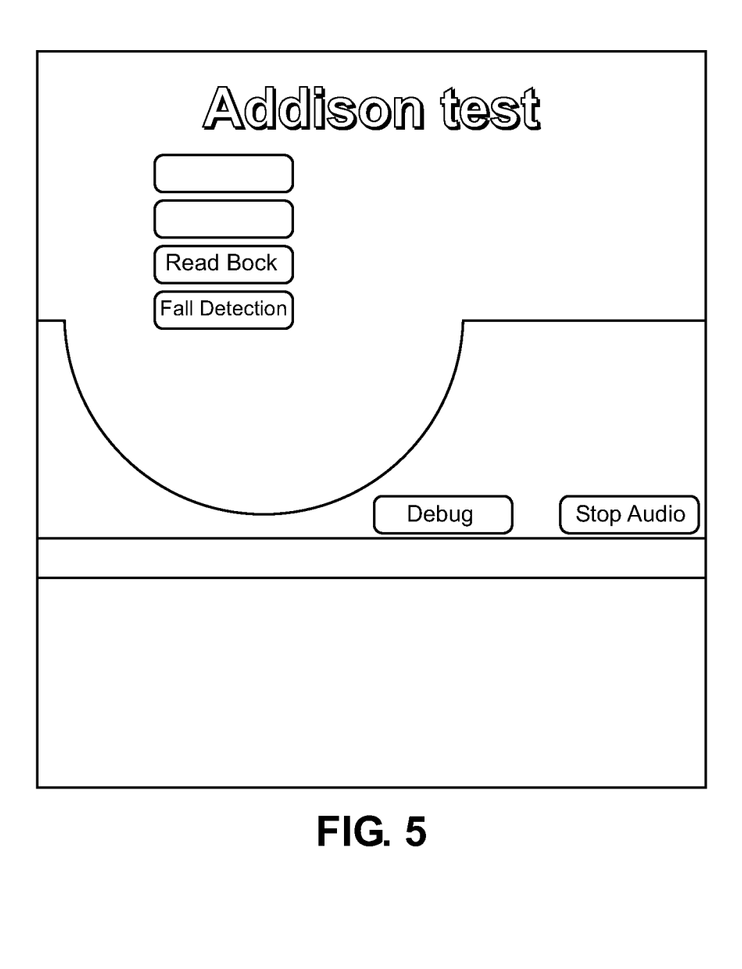
FIG. 5 is a test demonstration of functioning actions connected via Lambda functions to a personal assistant service, activated via voice prompt. These buttons are unseen by the end user of the system but utilized to connect the Electronic Caregiver Image to the Electronic Caregiver Optimum Recognition Blueprint and personal assistant services.
Figure 6:
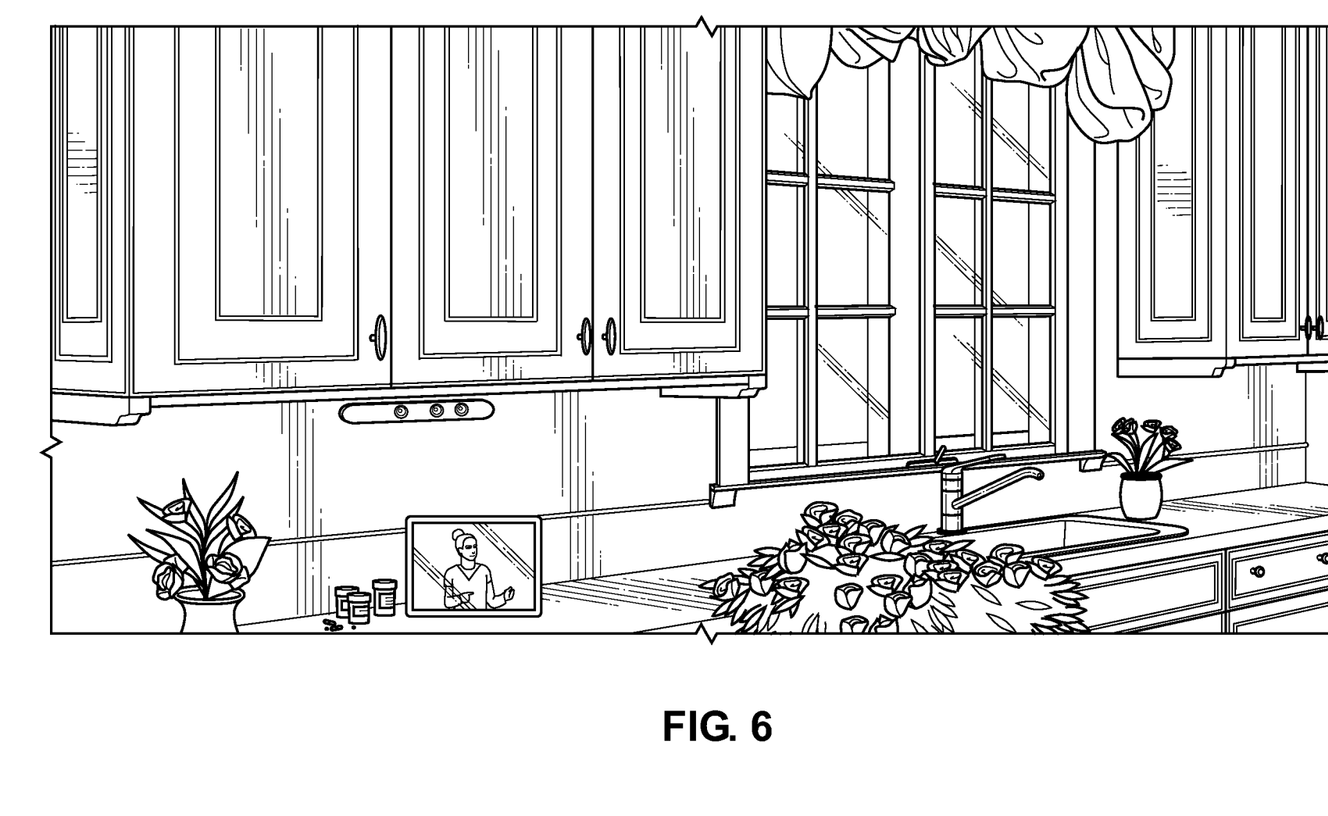
FIG. 6 is an illustration of one embodiment of the present invention, where an Electronic Caregiver Image named Addison appears on a tablet below a depth camera inside a home, ready to monitor the well-being of the end-user and communicate with them.
Figure 7:
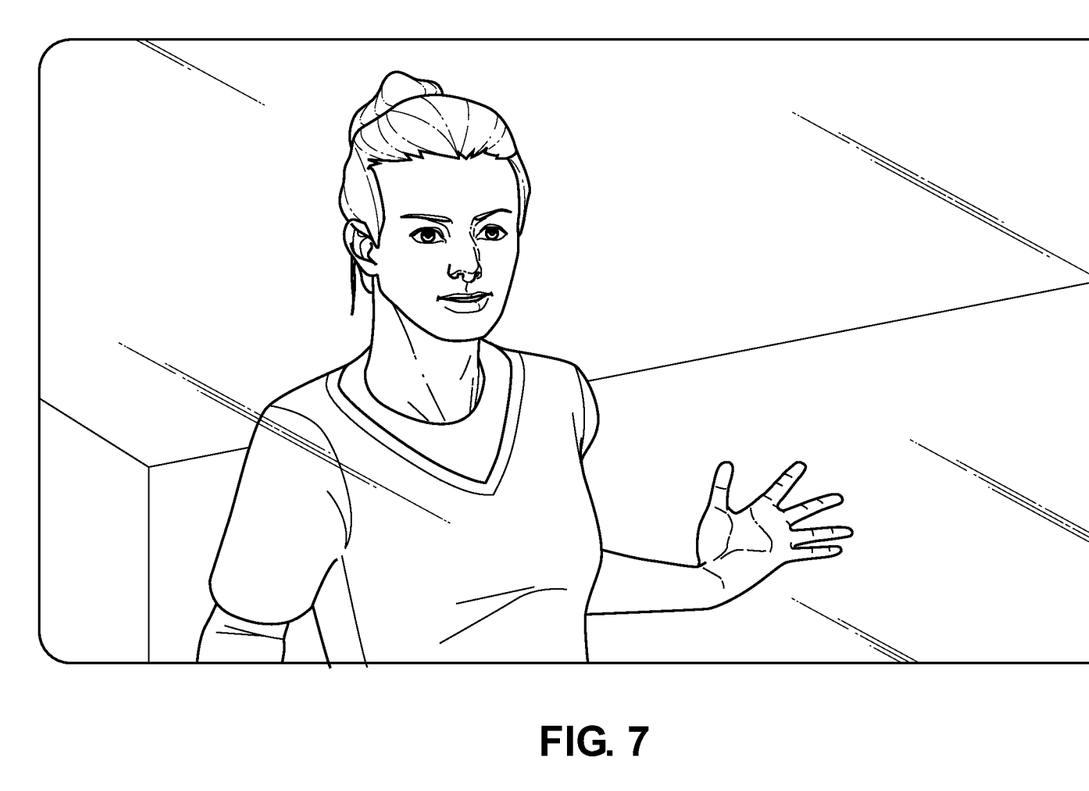
FIG. 7 is an illustration of one embodiment of the present invention, where an Electronic Caregiver Image named Addison speaks to an end-user regarding the status of a user's medication compliance schedule.

The back end of the Electronic Caregiver is the Optimum Recognition Blueprint ("ORB") depicted as item 1 in FIG. 2. The ORB is a mapped structure of models, objects, scripts, connections, and programs which manage users, devices, and data. The ORB may include connections which add mapping of additional objects and data obtained from responders or assessment parties such as monitoring services, customer services, health services, and insurance, as depicted in FIG. 2, item 7. Data received by the ORB from the Electronic Caregiver front end, including software applications running on portable devices (FIG. 2, item 8) is mapped to the appropriate data location and is responded to, compared, interpreted, analyzed, shared, or stored based upon the model of behaviors. (FIG. 2, item 17).

The data extracted from visual detection and other motion based devices are interpreted by the ORB. The ORB determines the appropriate method for processing the data received from the device and determines the customer identification data specific to that device (FIG. 2, item 11). For example, the ORB can determine whether the data is received from a sensor such as an accelerometer (FIG. 2, item 10), a newly connected depth camera or simply device data such as low battery life on a mobile phone. In the event the ORB detects low battery life, it can issue a warning to the user and communicate with other responsible parties to alert them that the connection with the Electronic Caregiver will be lost unless the device is charged. (FIG. 2, item 15).

The ORB can initiate an emergency call to action (FIG. 2, item 2) which includes communicating to a monitoring central station (FIG. 2, item 7) the necessary information to dispatch emergency services. The ORB can initiate technical support calls as well. (FIG. 2, item 5). These types of action include equipment trouble signals. (FIG. 2, item 3). The ORB can initiate a message to immediate users on location with the front end of the system (FIG. 2, item 4) and to external parties (FIG. 2, item 7) to provide diagnosis and warning of patterns of pain, distress, injury, incapacitation, inactivity, impaired activity, mortality, medical emergency, increased or decreased risk of fall, improving health related behavioral patterns, and other wellness/treatment plans.

In one embodiment, the present invention may include visual recognition hardware such as video cameras, depth cameras, infrared cameras, thermal cameras, proximity detectors, motion capture devices (FIG. 2, item 10).

The visual recognition firmware is systematically integrated upon ORB objects containing the unique models of the present invention (FIG. 2, item 15) that utilize the Electronic Caregiver's algorithms to detect and identify physical characteristics that may indicate various musculoskeletal, cardiac, and neurological events or patterns of gait or movement. Methodology is also capable of utilizing data from visual recognition devices to detect environmental hazards including stoves, ovens, and appliances reaching unsafe temperatures or left on unattended, laundry room and kitchen fires, and unsafe ambient temperatures. Certain data identified and processed can be communicated to end users, health service providers, live caregivers, and industrial or scientific parties.

Depth cameras provide the ORB with two data sets, one that is based upon movement markers assigned to the head, spine, and joint locations, and a second data set that is based upon volume. This data is then processed through the Electronic Caregiver to assign meaning.

In addition to observing gait changes over time and creating alerts when markers are observed the ORB can create alerts when an accidental fall occurs. Data observed through a depth camera with accidental falls are two dimensional observations of rapid acceleration in movement markers followed by rapid deceleration, which can be coupled with rapid change in direction. (FIG. 3). Depth camera data provides a third method of accidental fall verification by looking for volume in the area of the observed fall over time.

In another embodiment of the present invention, the ORB is connected to portable or wearable devices such as a Bluetooth® emitting beacon, mobile phones, wearable video recorders, wearable fitness and activity devices, and other health related devices, and may use wired or wireless pathways of communication between it and the devices. (FIG. 2, item 8).

Using an installed Electronic Caregiver software application and associated ORB objects containing data processing models utilizing algorithms, a variety of alerts, signaling parameters, one way and two way communications can be programmed and initiated, including summoning response when patterns of activity become irregular or suspicious.

In another embodiment of the present invention, ORB objects contain models to process and present an Electronic Caregiver Image ("ECI") (FIG. 2, item 6). The ECI utilizes ORB objects containing processing capabilities of a personal assistant including the capability to leverage and integrate with third party personal assistant systems. The ECI appears as an animated figure emulating a live action caregiver, and is presented on tablets with cameras that provide visual recognition described above while running firmware connected to Electronic Caregiver back end systems. The ECI also appears on media or video screens, or devices containing presentation capability, such as mobile phones, wearable devices, and existing television or computer monitors. The ECI may appear in strictly auditory format in applications where this is found to better meet user or platform needs.

The ECI may provide dietary or medication reminders, appointment reminders, and may act as a sincere, caring or humorous companion. The ECI can present companionship, and identify and display medications or health test equipment, and can engage in an exchange between device and end user that results in an experience that appears life like and intelligent. The ECI relies upon the Electronic Caregiver ORB system and algorithms, and may learn end user behaviors, likes and dislikes, resulting in modified preprogrammed behaviors and a more pleasing interactive experience.

The ECI interface and algorithms may receive input from 2-way audio and/or visual devices. When visual or audio devices detect a need for intervention, the ECI can respond to verbal and physical cues from the end user and may respond accordingly, including initiating a video, audio or other method of dialog between the end user and an external party. ECI features, security and permissions are established using a simple applications based user interface.

In another embodiment of the present invention Electronic Caregiver ORB systems are connected to visual or audio recognition devices, or heat and fluid sensors, and can detect and signal the Electronic Caregiver front end and the ORB in response to running water, fire, temperature, status of appliances, and may also detect movement and the opening of windows and doors. Detection of the above mentioned conditions may result in communications initiated to the end user or third parties.

In another embodiment of the present invention, the ORB is connected through the Electronic Caregiver front end to devices such as visual or audio recognition devices, or pressure or sensors that can detect the opening or closing of containers. Using the Electronic Caregiver algorithms, the sensing devices can monitor a medication organizer or dispenser and record usage, dosage, or may warn if the end user is attempting to access the wrong medication or dosage.

In another embodiment of the present invention, the Electronic Caregiver back end is connected through the Electronic Caregiver front end to devices such as mobile phones or portable/wearable activity or health monitoring devices, providing a Health Direct Link and integrated application. The Electronic Caregiver algorithms and applications provide an easy to access one touch feature to access an immediate link to an external third party during a medical emergency, and geo-positioning monitoring may be activated to locate the end user. This feature provides an option by mode selection of the application to initiate non-emergency connections to an external third party such as a health professional or emergency responder during a medical concern such as trouble breathing, trouble swallowing, head pain, abdominal pain or an escalation in these conditions.

The ECI will include a standard of care assessment module. Through an automated, integrated array of stationary and at least one of a wearable technology sensor or detector, such as ground reaction sensing, medical peripherals which may include thermometer, blood pressure device, glucometer, pulse 02 sensor, weight scale, spirometer, glucometer, digital camera, laser, depth and thermal cameras, and at least one facial or body recognition interpretive device, verbal, audible and physical feedback systems, and a display monitor or projection. The system will monitor and assess symptoms and indicators of improvement, stability or decline to physical or mental health status. The system uses a combination of artificial caregiver projected or displayed imagery, and natural language engines, coupled with artificial intelligence software, machine learning and at least one of an in-home or on-body device to monitor and enable real time patient assessments, interventions and reports. The system is used to supplement or replace a live physical caregiver to prompt, analyze and respond to both standard and proprietary symptomatic diagnostic formulas.

The system identifies and interprets health symptoms and status indicators such as hydration, bathroom usage and type, wake and sleep patterns, activity and inactivity characteristics and type, biomechanical and movement diagnostics, mood and mental state assessments, dietary and nutrition activity, vital readings and statistics, interrogatory responses and both standard and non-standard indicators necessary to monitor health performance, stability or decline. Real time monitoring is uploaded into real time cloud diagnostic and assessment software to interpret required responses and interventions to recommend or implement methods of care, suggested improvements to standards of care, to identify non-working methods and standards of care, to compare and evaluate various standards of care, and to notify and report to specific or interdisciplinary parties that can engage to improve patient health and wellness outcomes. System may also be programmed to advise and inform technology, pharmacology, device, software or physical care providers or parties of relevant data for the purposes of disclosing poor performance products, services or patient responses, as well as improvements, trends and recommendations to compel advanced innovation for patient care and service.

In one embodiment of the present invention, ORB initiates shipment of a pharmacogenetic saliva sample kit as soon as a Virtual Caregiver System (VCS), a tablet & depth camera combination system featuring the ECI, is placed on order. The patient will be prompted by the ECI and shown instructions by the ECI on how to complete the swab and saliva sample and mail the kit to the lab. The lab conducts the genetic screening and will electronically forward a report to the ORB to store the genetic profile information and results. The ECI alerts the patient via home care alerts and tablets, and conducts the pharmacology consultation with the patient, making recommendations on updating their medications if necessary based on test results, and metabolic drug scoring. Replacement medications are then entered or scanned into the ORB using the localized ECI, and recognized by the software as a replacement drug, whereby the reminders and monitoring system is updated. A report is available to print for primary care physician, pharmacist or related health specialist.

In another embodiment of the present invention, the ORB is connected through the Electronic Caregiver front end to devices such as mobile phones, computers or tablets, onto which is displayed a Comprehensive Falls Risk Screening Instrument ("CFRSI"), which includes proprietary algorithms to process user information inputs to produce a diagnostic output. THE CFRSI uses a process to collect history information, range of motion data, and other key indicators to identify and publish a fall risk profile and assessed score and grading profile. This data is then referenced against other pertinent data collected from the end user's mobile phone, wearable device, or information collected from visual recognition devices or pressure sensing devices.

In another embodiment, the ORB collects and stores data in cumulative storage locations. Machine learning algorithms are then incorporated to assess data received from all participating end users. All is compared and processed to output information to improve health awareness.

While the preferred embodiments have been shown and described, it will be understood that there is no intent to limit the invention by such disclosure, but rather, is intended to cover all modifications and alternate constructions falling within the spirit and scope of the invention as defined in the appended claims.

The invention claimed is:

1. A method for automated fall detection and reporting via a virtual system, the virtual system comprising at least one processor configured to execute the method comprising:

receiving, at the at least one processor in the virtual system, from a depth camera configured to be pointed at a human, a first data set of virtual movement markers comprising a cluster of data points in a shape of a body of the human, the first data set of virtual movement markers comprising a first movement marker estimated to a head location of the human, a second movement marker estimated to a spine location of the human, and a third movement marker estimated to a joint location of the human;

receiving, at the at least one processor in the virtual system, from the depth camera a second data set of virtual movement markers indicating volume in an area of a location of the human:

detecting, at the at least one processor in the virtual system, a first irregular pattern of activity for the human based on the volume in the area of the location of the human over a prescribed period of time;

sending, at the at least one processor in the virtual system, a first alert to a reporting device indicating that the human has fallen based on the detection of the first irregular pattern of activity;

detecting, at the at least one processor in the virtual system, from an accelerometer, a rapid acceleration of at least two of the movement markers comprising the first data set of virtual movement markers, followed by a rapid deceleration of the at least two of the movement markers comprising the first data set of virtual movement markers, wherein at least one of the rapid acceleration and the rapid deceleration includes a rapid change in direction of a location of at least one of the movement markers comprising the first data set of virtual movement markers;

detecting, at the at least one processor in the virtual system, a second irregular pattern of activity for the human from changes in the first data set of virtual movement markers; and sending, at the at least one processor in the virtual system, a second alert to the reporting device indicating that the human has fallen based on the second detected irregular pattern of activity.

2. The method of claim 1, further comprising processing the first data set and the second data set from the depth camera against an optimum recognition blueprint.

3. The method of claim 1, wherein the first and the second alerts to the reporting device comprise a communication from the virtual system to a monitoring central station with necessary information to dispatch local emergency services to the location of the human.

4. The method of claim 1, wherein the first and the second alerts to the reporting device comprise a communication from the virtual system to a user computing device warning that the human has fallen.

5. The method of claim 1, the head location of the human comprising an initial depth position of a head, an initial vertical position of the head, and an initial horizontal position of the head.

6. The method of claim 1, the detecting of the rapid acceleration of the at least two of the movement markers further comprising detecting a change in an initial depth position of a head, detecting a change in an initial vertical position of the head, and detecting a change in an initial horizontal position of the head.

7. The method of claim 1, further comprising plotting a change in an initial depth position of a head, a change in an initial vertical position of the head, and an initial horizontal position of the head against a time measurement.

8. The method of claim 1, further comprising transmitting the alert to the reporting device when a predefined threshold is exceeded by a plotting of a change in an initial depth position of a head, a change in an initial vertical position of the head, or a change in an initial horizontal position of the head against a time measurement.

9. The method of claim 1, further comprising adjusting a predefined threshold when a fall does not result.

10. A system for automated fall detection and reporting, the system comprising:
a camera communicatively coupled to at least one processor, the camera configured to be pointed at a human;
an accelerometer communicatively coupled to the at least one processor;
a reporting device communicatively coupled to the at least one processor; and the at least one processor configured to execute a method comprising:
receiving a first data set of virtual movement markers comprising a cluster of data points in a shape of a body of a human, the first data set of virtual movement markers comprising a first movement marker estimated to a head location of the human, a second movement marker estimated to a spine location of the human, and a third movement marker estimated to a joint location of the human;
receiving a second data set, from the camera, indicating volume in an area of a location of the human;
detecting a first irregular pattern of activity for the human based on the indicated volume in the area of the location of the human over a prescribed period of time;
sending, at the at least one processor in the virtual system, a first alert to a reporting device indicating that the human has fallen based on the detection of the irregular pattern;
detecting, by the accelerometer, a rapid acceleration of at least two of the movement markers comprising the first data set of virtual movement markers, followed by a rapid deceleration of the at least two of the movement markers comprising the first data set of virtual movement markers, wherein at least one of the rapid acceleration and the rapid deceleration includes a rapid change in direction of a location of at least one of the movement markers comprising the first data set of virtual movement markers;
detecting a second irregular pattern of activity for the human from changes in the first data set of virtual movement markers; and
sending second alert to the reporting device indicating that the human has fallen based on the second detected irregular pattern of activity.

11. The system of claim 10, wherein the camera comprises one of a video camera, a depth camera, an infrared camera, a thermal camera, a proximity detector, and a motion capture device.

12. The system of claim 10, wherein the at least one processor is further configured to process the first data set and the second data set from the camera against an optimum recognition blueprint.

13. The system of claim 10, wherein the first and the second alerts to the reporting device comprise a communication to a monitoring central station with necessary information to dispatch local emergency services to the location of the human.

14. The system of claim 10, wherein the first and the second alerts to the reporting device comprise a communication to a user computing device warning that the human has fallen.

15. The system of claim 10, wherein the head location of the human comprises an initial depth position of a head, an initial vertical position of the head, and an initial horizontal position of the head.

16. The system of claim 10, wherein the detecting of the rapid acceleration of the at least two of the movement markers further comprises detecting a change in an initial depth position of a head, detecting a change in an initial vertical position of the head, and detecting a change in an initial horizontal position of the head.

17. The system of claim 10, wherein the at least one processor is further configured to plot a change in an initial depth position of a head, a change in an initial vertical position of the head, and a change in an initial horizontal position of the head against a time measurement.

18. A non-transitory processor-readable medium having instructions stored thereon which when executed by one or more processors, cause the one or more processors to implement a method for automated fall detection, the method comprising:
    receiving, from a depth camera configured to be pointed at a human, a first data set of virtual movement markers comprising a cluster of data points in a shape of a body of the human, the first data set of virtual movement markers comprising a first movement marker estimated to a head location of the human, a second movement marker estimated to a spine location of the human, and a third movement marker estimated to a joint location of the human;
    receiving, from the depth camera, a second data set indicating volume in an area of a location of the human:
    detecting a first irregular pattern of activity for the human based on the volume in the area of the location of the human over a prescribed period of time;
    sending a first alert to a reporting device indicating that the human has fallen based on the detection of the first irregular pattern of activity;
    detecting, from an accelerometer, a rapid acceleration of at least two of the movement markers comprising the first data set of virtual movement markers, followed by a rapid deceleration of the at least two of the movement markers comprising the first data set of virtual movement markers, wherein at least one of the rapid acceleration and the rapid deceleration includes a rapid change in direction of a location of at least one of the movement markers comprising the first data set of virtual movement markers;
    detecting an irregular pattern of activity for the human from changes in the first data set of virtual movement markers and the second data set; and
    sending a second alert to a reporting device indicating that the human has fallen based on the detected irregular pattern of activity.

19. The non-transitory processor-readable medium of claim 18, further comprising processing the first data set and the second data set from the depth camera against an optimum recognition blueprint.

20. The non-transitory processor-readable medium of claim 18, the method further comprising transmitting the first and the second alerts to the reporting device when a predefined threshold is exceeded by one of a measurement of a change in an initial depth position of a head, a change in an initial vertical position of the head, or a change in an initial horizontal position of the head against a time measurement.

* * * * *